US011366071B2

(12) United States Patent
Alvarez

(10) Patent No.: US 11,366,071 B2
(45) Date of Patent: *Jun. 21, 2022

(54) PERFORMING MICROWAVE MEASUREMENTS ON SAMPLES UNDER CONFINING PRESSURE USING COAXIAL RESONATORS

(71) Applicant: Saudi Arabian Oil Company, Dhahran (SA)

(72) Inventor: Jose Oliverio Alvarez, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 197 days.

This patent is subject to a terminal disclaimer.

(21) Appl. No.: 16/808,956

(22) Filed: Mar. 4, 2020

(65) Prior Publication Data

US 2021/0278351 A1 Sep. 9, 2021

(51) Int. Cl.
*G01N 22/04* (2006.01)
*E21B 47/117* (2012.01)
(Continued)

(52) U.S. Cl.
CPC ............. *G01N 22/04* (2013.01); *E21B 21/08* (2013.01); *E21B 47/07* (2020.05); *E21B 47/117* (2020.05); *E21B 49/08* (2013.01); *E21B 49/0875* (2020.05)

(58) Field of Classification Search
CPC .... G01N 22/00; G01N 22/04; G01N 33/2823; G01N 27/026; G01N 33/28; E21B 21/08;
(Continued)

(56) References Cited

U.S. PATENT DOCUMENTS 2,558,427 A 6/1951 Fagan
3,434,046 A 3/1969 Wilson et al.
(Continued)

FOREIGN PATENT DOCUMENTS

GB 2110377 6/1983
WO WO 0201211 1/2002

OTHER PUBLICATIONS

PCT International Search Report and Written Opinion in International Appln. No. PCT/US2021/020479, dated Jun. 22, 2021, 13 pages.
(Continued)

*Primary Examiner* — Nimeshkumar D Patel
*Assistant Examiner* — Jean F Morello
(74) *Attorney, Agent, or Firm* — Fish & Richardson P.C.

(57) ABSTRACT

A pressure cell system includes a pressure cell configured to house a sample within inner walls of the pressure cell. An injectable medium is injected by an injection system of the pressure cell system into the pressure cell in a gap between the sample and the inner walls. The injectable medium in the pressure cell is heated by a heating element of the pressure cell system. A pressure inside the pressure cell is measured by a pressure gauge of the pressure cell system. A temperature in the pressure cell is measured by a temperature gauge of the pressure cell system. Microwave permittivity measurements of the sample are captured by a coaxial resonator system of the pressure cell system. The microwave permittivity measurements of the sample are captured at different combinations of temperatures and pressures. The microwave permittivity measurements include measurements of permittivity of gas under pressure at plural frequencies.

11 Claims, 4 Drawing Sheets

(51) Int. Cl.
*E21B 47/07* (2012.01)
*E21B 21/08* (2006.01)
*E21B 49/08* (2006.01)

(58) Field of Classification Search
CPC ........ E21B 47/07; E21B 47/117; E21B 49/08; E21B 49/0875
See application file for complete search history.

(56) References Cited

U.S. PATENT DOCUMENTS

| | | | |
|---|---|---|---|
| 3,498,112 | A | 3/1970 | Howard |
| 3,681,684 | A | 8/1972 | Busker et al. |
| 3,815,019 | A | 6/1974 | Wiles |
| 5,014,010 | A | 5/1991 | Helms |
| 5,188,837 | A | 2/1993 | Domb |
| 5,351,521 | A | 10/1994 | Cracknell |
| 5,455,516 | A | 10/1995 | Buford et al. |
| 5,720,345 | A | 2/1998 | Price et al. |
| 6,084,403 | A | 7/2000 | Sinclair et al. |
| 6,333,699 | B1 | 12/2001 | Zierolf |
| 6,411,084 | B1 | 6/2002 | Yoo |
| 6,534,980 | B2 | 2/2003 | Toufaily et al. |
| 6,768,299 | B2 | 7/2004 | Almaguer |
| 7,049,272 | B2 | 5/2006 | Sinclair et al. |
| 7,376,514 | B2 | 5/2008 | Habashy et al. |
| 7,628,058 | B2 | 12/2009 | Vinci |
| 8,237,444 | B2 | 8/2012 | Simon |
| 8,794,062 | B2 | 8/2014 | DiFoggio et al. |
| 8,884,624 | B2 | 11/2014 | Homan et al. |
| 8,916,815 | B2 | 12/2014 | Xie et al. |
| 9,562,987 | B2 | 2/2017 | Guner et al. |
| 2006/0016592 | A1 | 1/2006 | Wu |
| 2007/0279073 | A1 | 12/2007 | Wee |
| 2008/0047337 | A1 | 2/2008 | Chemali et al. |
| 2010/0270291 | A1 | 10/2010 | Kotzian et al. |
| 2013/0002258 | A1* | 1/2013 | Ligneul .................. E21B 47/06 324/376 |
| 2013/0009048 | A1* | 1/2013 | Xie ........................ G01N 21/33 250/256 |
| 2013/0110411 | A1 | 5/2013 | Black et al. |
| 2013/0125630 | A1* | 5/2013 | Collins .................. E21B 43/20 73/64.56 |
| 2013/0283892 | A1 | 10/2013 | Parker |
| 2014/0291023 | A1 | 10/2014 | Edbury |
| 2016/0237810 | A1 | 8/2016 | Beaman et al. |
| 2016/0320769 | A1 | 11/2016 | Deffenbaugh et al. |
| 2016/0334343 | A1 | 11/2016 | Hurlimann et al. |
| 2017/0248530 | A1 | 8/2017 | Parker et al. |
| 2018/0187498 | A1 | 7/2018 | Soto et al. |
| 2019/0346378 | A1 | 11/2019 | Alvarez |

OTHER PUBLICATIONS

U.S. Appl. No. 15/045,362, filed Aug. 18, 2016, Beaman et al.
U.S. Appl. No. 15/397,247, filed Jul. 5, 2018, Soto et al.
"Anton-Paar Pressure Cell Manual," Pressure Cell PR170/Ti/XL and PR170/Ha/XL, Jul. 2017, 34 pages.
Aakre et al., "Conductivity and Permittivity of Midel 7131: Effect of Temperature, Moisture Content, Hydrostatic Pressure and Electric Field," IEEE Transactions on Dielectrics and Electrical Insulation, vol. 23, No. 5, Oct. 2016, 8 pages.
Carpenter, "Advancing Deepwater Kick Detection", JPT, vol. 68, Issue 5, May 2016, 2 pages.
Garcia-Banos et al., "Non-Invasive Monitoring of Polymer Curing Reactions by Dielectrometry," IEEE Sensors Journal, vol. 11, No. 1, Jan. 2011, 9 pages.
Johnson et al., "Advanced Deepwater Kick Detection," IADC/SPE 167990, presented at the 2014 IADC/SPE Drilling Conference and Exhibition, Mar. 4-6, 2014, 10 pages.
Karimi et al., "Design and Dynamic Characterization of an Orientation Insensitive Microwave Water-Cut Sensor" IEEE Microwave Theory and Technique, Jun. 12, 2017, vol. 66, Issue 1, Jan. 2018, 10 pages.
Oliverio et al., "Dielectric characterization of geochemical properties of crude oils and gas condensate at 25degrees C.," 2017 IEEE International Geoscience and Remote Sensing Symposium (IGARSS), IEEE, Jan. 23, 2017, 4 pages.
Olver, "Compact Antenna Test Ranges," Seventh International Conference on Antennas and Propagation IEEE, Apr. 15-18, 1991, 10 pages.
Parini et al., "Chapter 3: Antenna measurements," in Theory and Practice of Modern Antenna Range Measurements, IET editorial, 2014, 30 pages.
Petrowiki.org [online], "Kicks," Petrowiki, available on or before Jun. 26, 2015, retrieved on Jan. 24, 2018, retrieved from URL <https://petrowiki.org/Kicks>, 6 pages.
Rayoteksightwindows.com [online], "High Pressure Flow Cell Signt Window," available on or before Mar. 2, 2018, retrieved on May 17, 2019, retrieved from URL <https://rayoteksightwindows.com/products/flowcell-sight-glass-windows-en.html>, 1 page.
Rigzone.com [online], "How does Well Control Work?" Rigzone, available on or before 1999, retrieved on Jan. 24, 2019, retrieved from URL <https://www.rigzone.com/training/insight.asp?insight_id=304&c_id>, 5 pages.
Stankowski et al., "Microwave resonators for EPR studies at high hydrostatic pressure," Review of Scientific Instruments, vol. 47, No. 1, Jan. 1, 1976, 3 pages.

* cited by examiner

PERFORMING MICROWAVE MEASUREMENTS ON SAMPLES UNDER CONFINING PRESSURE USING COAXIAL RESONATORS

TECHNICAL FIELD

The present disclosure applies to capturing measurements of a sample in a pressure cell.

BACKGROUND

Measuring certain properties of materials at downhole conditions, such as in oil wells, can be challenging. Conventional systems use high-pressure cells, for example, by putting a sample under pressure to measure maximum shear stresses. Conventional systems typically perform a few measurements that are limited to only one frequency and temperature.

SUMMARY

The present disclosure describes techniques that can be used to perform microwave measurements on samples under confining pressure and using coaxial resonators. In some implementations, a pressure cell system includes a pressure cell configured to house a sample within inner walls of the pressure cell. An injectable medium is injected by an injection system of the pressure cell system into the pressure cell in a gap between the sample and the inner walls. The injectable medium in the pressure cell is heated by a heating element of the pressure cell system. A pressure inside the pressure cell is measured by a pressure gauge of the pressure cell system. A temperature in the pressure cell is measured by a temperature gauge of the pressure cell system. Microwave permittivity measurements of the sample are captured by a coaxial resonator system of the pressure cell system. The microwave permittivity measurements of the sample are captured at different combinations of temperatures and pressures. The microwave measurements include measurements of permittivity of gas under pressure at plural frequencies.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/the instructions stored on the non-transitory, computer-readable medium.

The subject matter described in this specification can be implemented in particular implementations, so as to realize one or more of the following advantages. First, the techniques of the present disclosure provide more realistic results than conventional techniques that simply: a) measure microwave properties (permittivity) at atmospheric pressure with other measurement equipment, b) perform polymer curing with no pressure, c) do not measure microwaves, or d) do not use quartz or sapphire windows to convert a window into a coaxial probe for a coaxial resonator. Second, conventional systems do not use high-frequency microwave properties at pressure.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

The following detailed description describes techniques for using a pressure cell that can make microwave measurements. The pressure cell can be used to make high-frequency measurements under high pressures and temperatures. A window in the pressure cell can be made with a strong dielectric material such as quartz or sapphire. The strong dielectric window can enable the pressure cell to withstand high temperatures and pressures while exhibiting stable dielectric properties for many temperatures. The dielectric material can be used as the dielectric of a coaxial resonator.

Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Figure 1:
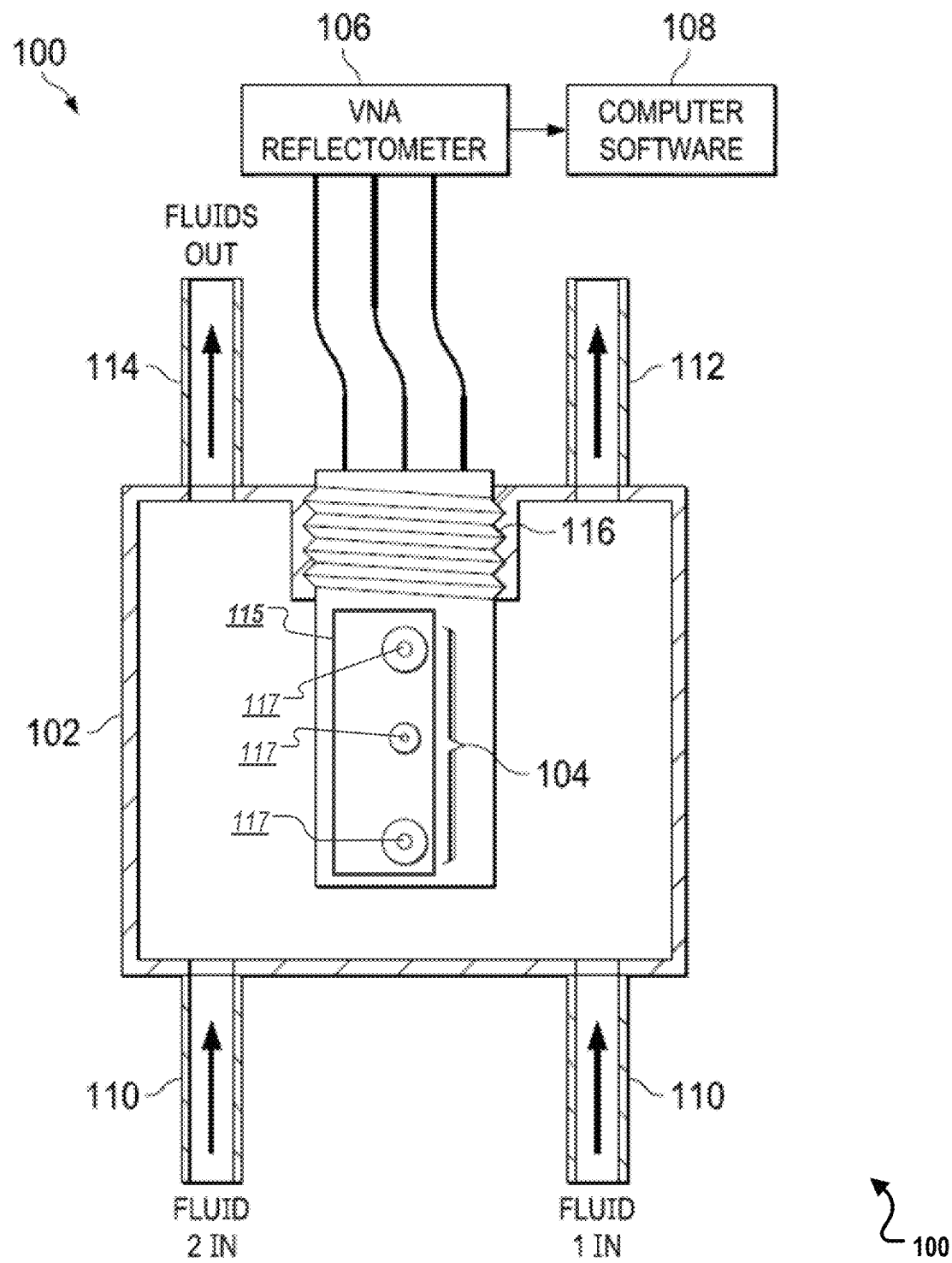
FIG. 1 is a block diagram showing an example of a pressure cell system, according to some embodiments of the present disclosure.

FIG. 1 is a block diagram showing an example of a pressure cell system 100, according to some embodiments of the present disclosure. The pressure cell system 100 includes a pressure cell 102 that can be used to perform measurements of samples that are placed in the pressure cell 102.

In some embodiments, the pressure cell 102 can be a confining pressure cell that is modified to allow for microwave measurements, for example, of (scattering) Sn parameters at different pressures and temperatures. A basic implementation consists of measuring the complex permittivity of a fluid or fluids filling the pressure cell. A modification can be based, at least in part, on designs for microwave sensor systems for noninvasive monitoring of curing processes.

The pressure cell 102 can be modified to allow for microwave measurements at different pressures and temperatures. The confining pressure cell can be part of a configuration that is combined with a microwave sensor system for the noninvasive monitoring of curing processes.

In some embodiments, the confining pressure cell can be modified to create the pressure cell 102. In one embodiment, an open coaxial probe can be added as part of the inner walls of the confining pressure cell by using available technologies of glass/metal fusion, for example, including quartz and metal. A high-pressure viewing window can be combined with a short-circuited coaxial probe, providing a coaxial resonator. One or more fixed open coaxial probes can be integrated within a coaxial resonator system that can include, for example, at least one coaxial resonator 104. The closed and sealed cell is filled with a fluid through an injection tube 110. As fluid injection continues, permittivity measurements at different frequencies can be obtained as the pressure rises.

In some implementations, the confining pressure cell can be manufactured using the following process. First, short-circuited coaxial line can be added as part of the inner walls of a confining pressure cell and filled with quartz or sapphire by using, for example, glass to metal fusion. The cell is closed and sealed and then filled with a fluid through the injection tube 110.

In some implementations, the confining pressure cell can be a stainless steel, cylindrical or cubic, pressure cell (with a fluid or gas injection system) that includes a pressure gauge, a heating element, and a temperature gauge. The internal diameter of the confining pressure cell can be just slightly larger than that of the solid samples.

In some implementations, when the sample is gas, the cell can first be closed, and the gas can be injected to remove air in the cell. In some implementations, when the sample is a gas, a vacuum can be created in the cell before the cell is filled with the desired gas. The gas can be injected until a desired combination of pressure and temperature is reached.

In some embodiments, the pressure cell 102 can be made of titanium or a mixture of metals. In some embodiments, the inner walls of the coaxial line and surface of the inner conductor can be coated with a silver or gold bath or coating for increased conductivity, such as before the quartz is added.

The internal walls of the cell can have at least one quartz or sapphire window. The window can have a circular shape and can include a central conductor. The dimensions of the central conductor diameter and the outer diameter of the quartz window can facilitate a coaxial line of a desired impedance (for example, 50 ohms).

The coaxial line can be a coaxial resonator that is ended by a short circuit (or wall). The coaxial line can be connected to a vector network analyzer (VNA) 106 or a miniaturized reflectometer. The VNA or the reflectometer can compute a resonance frequency and a quality factor. A permittivity can be computed from the resonance frequency and the quality factor. The computed permittivity can be used in developing downhole tools used to characterize different geochemical properties.

In some implementations, the window can be a transmission line. The transmission line can be used with fluid samples under pressure. The transmission line can use a different kind of software than that typically used for coaxial resonators.

The output of the VNA/reflectometer 106, including $S_{11}$ parameter measurements of a sample in the pressure cell 102, can be provided to computer software 108 to obtain the complex permittivity of the sample at a particular frequency. For example, a user of a computing device on which the computer software 108 executes can review information about pressure, temperature, and microwave measurements in a graphical user interface (GUI) provided by the computer software 108. The computer software 108 can provide controls that the user can use to set a desired pressure and a desired temperature. An injection system and a heating element in the pressure cell 102 can attain and maintain the desired pressure and the desired temperature.

The pressure cell 102 can include at least two injection tubes 110 that are each capable for use in injecting gas or fluid into the pressure cell 102. In some embodiments, the pressure cell 102 can include a relief valve 112 that can be connected to a large sealed container for the recovery of fluid that passes through the relief valve 112. The relief valve 112 can include a pressure gauge for indicating the pressure inside the pressure cell 102. Release of gas or fluid can occur (for example, automatically) when the pressure cell 102 attains a pressure above a pre-determined threshold (for example, set by a user or by software). In some embodiments, the relief valve 112 can be activated manually. One of the injectors of the pressure cell 102 can be a fluid/pressure relief system. A high-pressure viewing window 115 of the pressure cell 102 includes short-circuited coaxial probes 117 connected to the coaxial resonators 104.

At least one output tube 114 can be connected to the pressure cell 102 and can be used to allow fluids to flow out of the pressure cell 102. The pressure cell 102 includes pressure threads 116. In some implementations, the pressure threads 116 can include a non-continuous thread (for example, using grooves) that are offset and can seal the pressure cell 102, including when the pressure cell 102 is pressurized.

Figure 2:
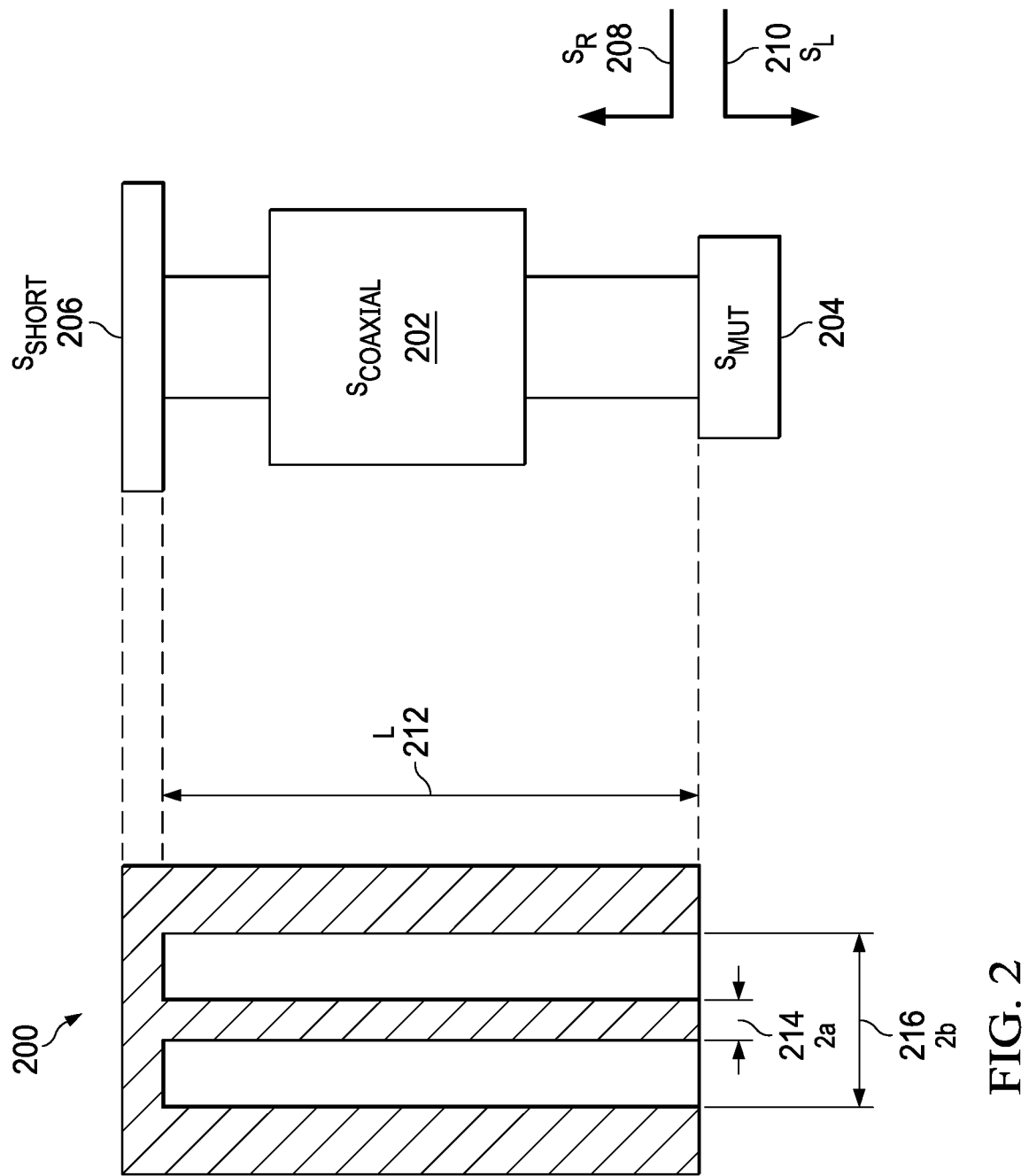
FIG. 2 is a drawing showing an example of a modeling of a microwave sensor system, according to some implementations of the present disclosure.

FIG. 2 is a drawing showing an example of a modeling of a microwave sensor system 200, according to some implementations of the present disclosure. The microwave sensor system 200 includes an interconnection with different scattering matrices, at both sides of the interface between the sensor and the material.

The scattering matrices include the following, for example. $S_{COAXIAL}$ 202 is the scattering matrix inside the coaxial line of the coaxial resonator. SMUT 204 is the scattering matrix inside the material under test (MUT) in contact with the open face of the coaxial resonator. $S_{SHORT}$ 206 is the scattering matrix at the shorted wall. $S_R$ 208 is the scattering matrix whose components reflect back into the coaxial line. $S_L$ 210 is the scattering matrix whose components are transmitted into the MUT. L 212 is the length of the coaxial line. Element $2a$ 214 is the diameter of the inner conductor. Distance $2b$ 216 is the diameter of the outer conductor.

Figure 3:
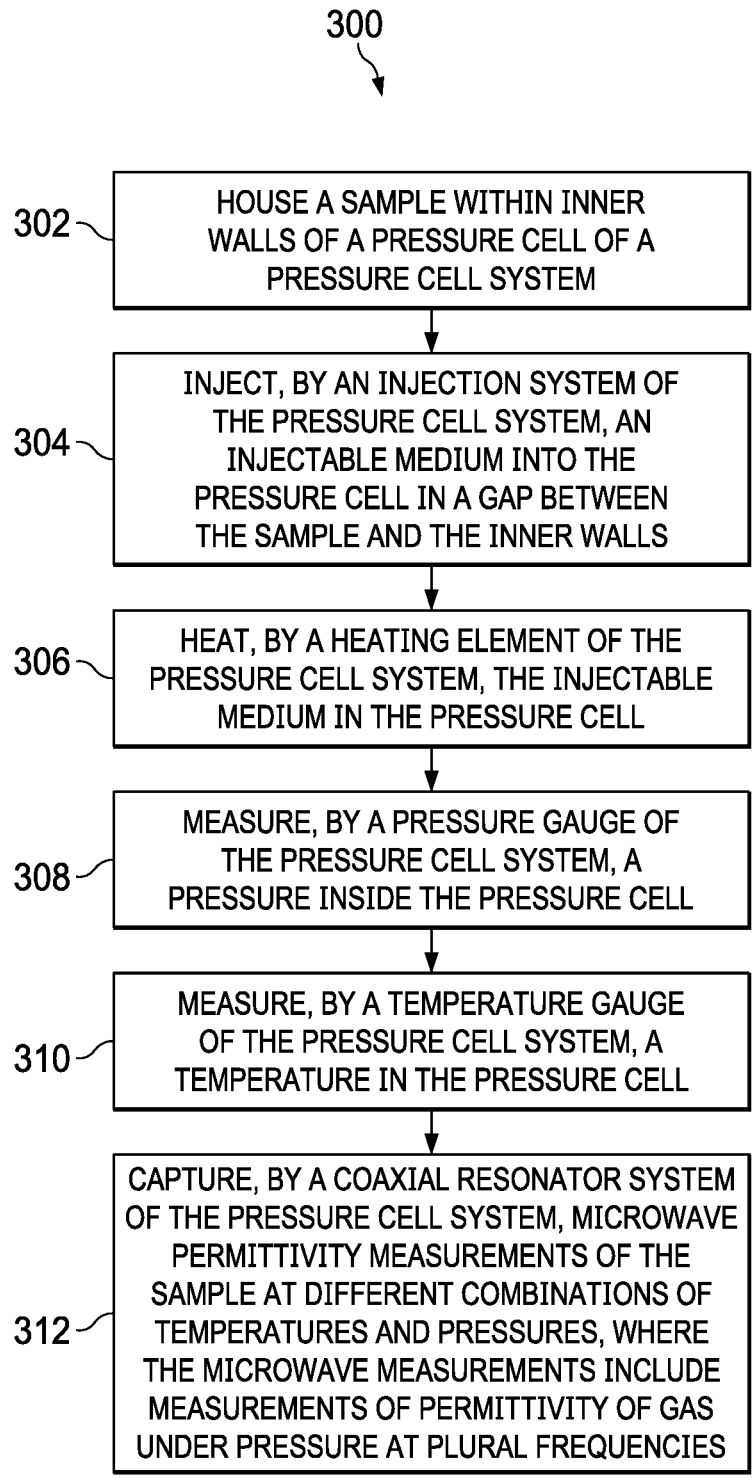
FIG. 3 is a flowchart of an example of a method for capturing measurements of a sample in a pressure cell system, according to some embodiments of the present disclosure.

FIG. 3 is a flowchart of an example of a method 300 for capturing measurements of a sample in a pressure cell system, according to some embodiments of the present disclosure. For example, the captured measurements include microwave permittivity measurements at different microwave frequencies and at different pressure and temperature combinations. For clarity of presentation, the description that follows generally describes method 300 in the context of the other figures in this description. However, it will be understood that method 300 may be performed, for example, by any suitable system, environment, software, and hardware, or a combination of systems, environments, software, and hardware, as appropriate. In some embodiments, various steps of method 300 may be run in parallel, in combination, in loops, or in any order.

At 302, a sample is housed within inner walls of a pressure cell of a pressure cell system. For example, the pressure cell 102 can house a sample that is to be measured by the pressure cell system 100. From 302, method 300 proceeds to 304.

At 304, an injectable medium is injected by an injection system of the pressure cell system into the pressure cell in a gap between the sample and the inner walls. As an example, an injectable medium, such as a fluid or a gas, can be injected into the pressure cell 102 through one or more of the injection tubes 110. The injectable medium can be injected into a gap between the sample and inner walls of the pressure cell 102. From 304, method 300 proceeds to 306.

At 306, the injectable medium in the pressure cell is heated by a heating element of the pressure cell system. For example, the pressure cell 102 can include a heating element that heats the sample in the pressure cell 102, such as by using heating elements at various locations on the inner walls of the pressure cell 102. From 306, method 300 proceeds to 308.

At 308, a pressure inside the pressure cell is measured by a pressure gauge of the pressure cell system. As an example, a pressure gauge of the pressure cell system 100 can measure pressures at one or more locations inside the pressure cell 102. From 308, method 300 proceeds to 310.

At 310, a temperature in the pressure cell is measured by a temperature gauge of the pressure cell system. For example, the pressure cell system 100 can include a temperature gauge that measures temperature at one or more locations inside a pressure cell. From 310, method 300 proceeds to 312.

At 312, microwave permittivity measurements of the sample are captured by a coaxial resonator system of the pressure cell system. The microwave permittivity measurements of the sample are captured at different combinations of temperatures and pressures. For example, the coaxial resonators 104 can capture microwave measurements after the sample is placed inside of the pressure cell 102 and the top of the pressure cell 102 is closed on the pressure cell. The microwave measurements can be captured after the injectable medium is injected into the pressure cell 102 in the gap between the sample and the inner walls. Heat can optionally be provided by the heating element to the injectable medium in the pressure cell 102. The microwave measurements include measurements of permittivity of gas under pressure at plural frequencies. For example, different frequencies of microwaves can be used at different combinations of pressure and temperature. After 312, method 300 stops.

In some implementations, method 300 can further include steps associated with user inputs provided in a user interface. For example, the computer software 108 can provide a user interface that supports operation of the pressure cell system 100 and the pressure cell 102. The user interface can receive user inputs specifying a pressure setting and a temperature setting to be achieved in the pressure cell system. Based on the received user inputs, the pressure cell system 100 can automatically adjust components (for example, heating elements) of the pressure cell system 100 to achieve desired pressure and temperature settings. The user interface can also display pressure information, temperature information, and captured microwave measurements of the sample.

Figure 4:
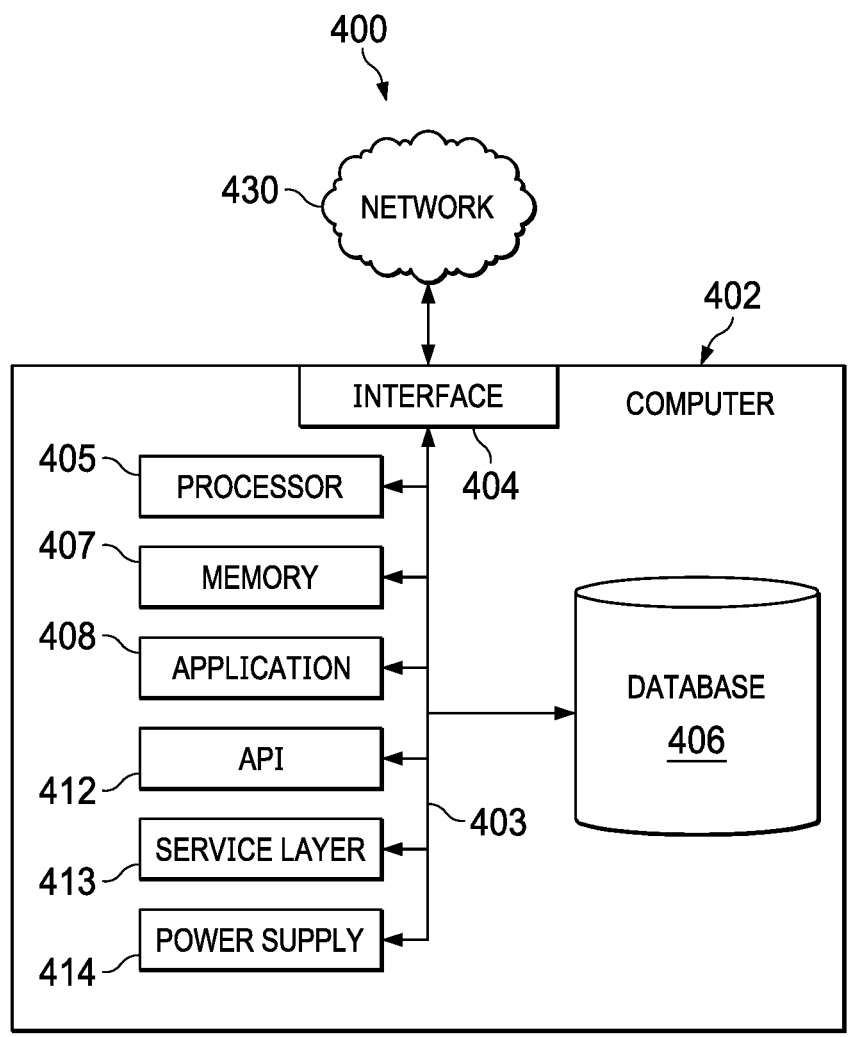
FIG. 4 is a block diagram illustrating an example computer system used to provide computational functionalities to implement techniques described in this disclosure.

FIG. 4 is a block diagram of an example computer system 400 used to provide computational functionalities to implement techniques described in this disclosure. The computational functionalities are associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a top level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both) over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the interface's hardware can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

Described implementations of the subject matter can include one or more features, alone or in combination.

For example, in a first implementation, a pressure cell system includes a pressure cell configured to house a sample within inner walls of the pressure cell. An injectable medium is injected by an injection system of the pressure cell system into the pressure cell in a gap between the sample and the inner walls. The injectable medium in the pressure cell is heated by a heating element of the pressure cell system. A pressure inside the pressure cell is measured by a pressure gauge of the pressure cell system. A temperature in the pressure cell is measured by a temperature gauge of the pressure cell system. Microwave permittivity measurements of the sample are captured by a coaxial resonator system of the pressure cell system. The microwave permittivity measurements of the sample are captured at different combinations of temperatures and pressures. The microwave permittivity measurements include measurements of permittivity of gas under pressure at plural frequencies.

The foregoing and other described implementations can each, optionally, include one or more of the following features:

A first feature, combinable with any of the following features, the coaxial resonator system further including: a heating element configured to provide heat to the injectable medium in the pressure cell; a pressure gauge configured to measure pressure inside the pressure cell; a pressure relief valve to release excess pressure above a specific threshold; and a temperature gauge configured to measure temperature in the pressure cell.

A second feature, combinable with any of the previous or following features, where the at least one fixed open coaxial probe is embedded in the inner walls using glass-metal fusion using quartz and a metal.

A third feature, combinable with any of the previous or following features, the system further including controls configured to allow setting, by a user, of a desired pressure and a desired temperature, wherein the injection system and the heating element are further configured to attain and maintain the desired pressure and the desired temperature.

A fourth feature, combinable with any of the previous or following features, the system further including a user interface configured to receive user inputs from a user, including pressure and temperature settings, and to display information about the pressure cell system, including pressure information, temperature information, and captured microwave permittivity measurements of the sample.

A fifth feature, combinable with any of the previous or following features, where the injectable medium is a fluid or a gas.

A sixth feature, combinable with any of the previous or following features, where the sample is a fluid sample, wherein, after the pressure cell is closed, the fluid sample is injected into the pressure cell to remove air in the pressure cell, and wherein injection of the gas sample continues until a desired pressure/temperature is attained.

A seventh feature, combinable with any of the previous or following features, where the sample is a fluid sample, wherein, after the pressure cell is closed, a vacuum is created in the pressure cell, and wherein the fluid sample is injected until a desired pressure/temperature is attained.

An eighth feature, combinable with any of the previous or following features, where the inner walls of the pressure cell include at least one quartz or sapphire filled, short-circuited, coaxial line.

A ninth feature, combinable with any of the previous or following features, where a diameter of a central conductor of the coaxial line and an outer diameter of a quartz window of the coaxial line provide dimensions supporting a coaxial line of a desired impedance.

A tenth feature, combinable with any of the previous or following features, where one end of the coaxial resonator system includes the coaxial line and is ended by a short circuit at an inner wall of the pressure cell, where the coaxial resonator system is connected to one of a vector network analyzer or a miniaturized reflectometer, and where the coaxial resonator system is configured to measure an $S_{11}$ reflection coefficient as a function of frequency for a given pressure and temperature from which an application computes a complex permittivity based on a resonant frequency a quality factor.

In a second implementation, a computer-implemented method includes the following. A sample is housed within inner walls of a pressure cell of a pressure cell system. An injectable medium is injected by an injection system of the pressure cell system into the pressure cell in a gap between the sample and the inner walls. The injectable medium in the pressure cell is heated by a heating element of the pressure cell system. A pressure inside the pressure cell is measured by a pressure gauge of the pressure cell system. A temperature in the pressure cell is measured by a temperature gauge of the pressure cell system. Microwave permittivity measurements of the sample are captured by a coaxial resonator system of the pressure cell system. The microwave permittivity measurements of the sample are captured at different combinations of temperatures and pressures. The microwave permittivity measurements include measurements of permittivity of gas under pressure at plural frequencies.

The foregoing and other described implementations can each, optionally, include one or more of the following features:

A first feature, combinable with any of the following features, where the microwave permittivity measurements are captured after: the sample is placed inside the pressure cell; a top including a pressure resistant lid is closed on the pressure cell; and the injectable medium is injected into the pressure cell in the gap between the sample and the inner walls.

A second feature, combinable with any of the previous or following features, where the microwave permittivity measurements are captured after heat is provided by the heating element to the injectable medium in the pressure cell.

A third feature, combinable with any of the previous or following features, the method further including: receiving, using a user interface of the pressure cell system, user inputs specifying a pressure setting and a temperature setting to be achieved in the pressure cell system; automatically adjusting, using the user inputs, components of the pressure cell system to achieve the pressure setting and the temperature setting; and displaying, using the user interface, pressure information, temperature information, and captured microwave permittivity measurements of the sample.

In a third implementation, a non-transitory, computer-readable medium storing one or more instructions executable by a computer system to perform operations including the following. A sample is housed within inner walls of a pressure cell of a pressure cell system. An injectable medium is injected by an injection system of the pressure cell system into the pressure cell in a gap between the sample and the inner walls. The injectable medium in the pressure cell is heated by a heating element of the pressure cell system. A pressure inside the pressure cell is measured by a pressure gauge of the pressure cell system. A temperature in the pressure cell is measured by a temperature gauge of the pressure cell system. Microwave permittivity measurements of the sample are captured by a coaxial resonator system of the pressure cell system. The microwave permittivity measurements of the sample are captured at different combinations of temperatures and pressures. The microwave permittivity measurements include measurements of permittivity of gas under pressure at plural frequencies.

The foregoing and other described implementations can each, optionally, include one or more of the following features:

A first feature, combinable with any of the following features, where the microwave permittivity measurements are captured after: the sample is placed inside the pressure cell; a top including a pressure resistant lid is closed on the pressure cell; and the injectable medium is injected into the pressure cell in the gap between the sample and the inner walls.

A second feature, combinable with any of the previous or following features, where the microwave permittivity measurements are captured after heat is provided by the heating element to the injectable medium in the pressure cell.

A third feature, combinable with any of the previous or following features, the operations further including: receiving, using a user interface of the pressure cell system, user inputs specifying a pressure setting and a temperature setting to be achieved in the pressure cell system; automatically adjusting, using the user inputs, components of the pressure cell system to achieve the pressure setting and the temperature setting; and displaying, using the user interface, pressure information, temperature information, and captured microwave permittivity measurements of the sample.

A fourth feature, combinable with any of the following features, where the injectable medium is a fluid or a gas.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A pressure cell system, comprising:
    a pressure cell configured to house a sample within inner walls of the pressure cell;
    a high-pressure viewing window of the pressure cell converted into at least one fixed open coaxial probe embedded in the inner walls of the pressure cell;
    an injection system configured to inject an injectable medium into the pressure cell in a gap between the sample and the inner walls;
    a top configured to provide a pressure resistant lid on the pressure cell; and
    a coaxial resonator system integrated with the at least one fixed open coaxial probe configured to capture microwave measurements of the sample at different combinations of temperatures and pressures, wherein the coaxial resonator system captures the microwave measurements after the sample is placed inside of the pressure cell, a top of the pressure cell is closed, and wherein the microwave measurements include the complex permittivity of gas under pressure at plural frequencies.

2. The pressure cell system of claim 1, wherein the coaxial resonator system further includes:
    a heating element configured to provide heat to the injectable medium in the pressure cell;
    a pressure gauge configured to measure pressure inside the pressure cell;
    a pressure relief valve to release excess pressure above a specific threshold; and
    a temperature gauge configured to measure temperature in the pressure cell.

3. The pressure cell system of claim 2, wherein the at least one fixed open coaxial probe is embedded in the inner walls using glass-metal fusion using quartz and a metal.

4. The pressure cell system of claim 2, further comprising controls configured to allow setting, by a user, of a desired pressure and a desired temperature, wherein the injection system and the heating element are further configured to attain and maintain the desired pressure and the desired temperature.

5. The pressure cell system of claim 1, further comprising a user interface configured to receive user inputs from a user, including pressure and temperature settings, and to display information about the pressure cell system, including pressure information, temperature information, and captured microwave measurements of the sample.

6. The pressure cell system of claim 1, wherein the injectable medium is a fluid or a gas.

7. The pressure cell system of claim 1, wherein the sample is a fluid sample, wherein, after the pressure cell is closed, the fluid sample is injected into the pressure cell to remove air in the pressure cell, and wherein a gas sample is injected into the pressure cell until a desired pressure/temperature is attained.

8. The pressure cell system of claim 1, wherein the sample is a fluid sample, wherein, after the pressure cell is closed, a vacuum is created in the pressure cell, and wherein the fluid sample is injected until a desired pressure/temperature is attained.

9. The pressure cell system of claim 1, wherein the inner walls of the pressure cell include at least one quartz or sapphire filled, short-circuited, coaxial line.

10. The pressure cell system of claim 9, wherein a diameter of a central conductor of the coaxial line and an outer diameter of a quartz window of the coaxial line provide dimensions which define a desired impedance of the coaxial line.

11. The pressure cell system of claim 10, wherein one end of the coaxial resonator system includes the coaxial line and is ended by a short circuit at an inner wall of the pressure cell, wherein the coaxial resonator system is connected to one of a vector network analyzer or a miniaturized reflectometer, and wherein the coaxial resonator system is configured to measure an $S_{11}$ reflection coefficient as a function of frequency for a given pressure and temperature from which an application computes a complex permittivity based on a resonant frequency a quality factor.

* * * * *